(12) United States Patent
Ryan

(10) Patent No.: US 10,912,582 B2
(45) Date of Patent: Feb. 9, 2021

(54) TROCAR DEVICE AND METHOD

(71) Applicant: Edwin Ryan, St. Paul, MN (US)

(72) Inventor: Edwin Ryan, St. Paul, MN (US)

(73) Assignee: Edwin Ryan, St. Paul, MN (US)

( * ) Notice: Subject to any disclaimer, the term of this patent is extended or adjusted under 35 U.S.C. 154(b) by 131 days.

(21) Appl. No.: 16/092,719

(22) PCT Filed: Apr. 12, 2017

(86) PCT No.: PCT/US2017/027202
§ 371 (c)(1),
(2) Date: Oct. 10, 2018

(87) PCT Pub. No.: WO2017/180739
PCT Pub. Date: Oct. 19, 2017

(65) Prior Publication Data
US 2019/0167300 A1 Jun. 6, 2019

Related U.S. Application Data

(60) Provisional application No. 62/321,571, filed on Apr. 12, 2016.

(51) Int. Cl.
*A61B 17/34* (2006.01)
*A61F 9/007* (2006.01)

(52) U.S. Cl.
CPC ...... *A61B 17/3421* (2013.01); *A61B 17/3417* (2013.01); *A61F 9/00736* (2013.01); *A61B 17/3462* (2013.01); *A61B 17/3496* (2013.01); *A61B 2017/346* (2013.01); *A61B 2017/3454* (2013.01)

(58) Field of Classification Search
CPC .......... A61B 17/320068; A61B 2017/320072; A61B 2017/320074; A61B 2017/320075; A61B 2017/320077; A61B 2017/32113; A61F 9/00736; A61F 9/00754
See application file for complete search history.

(56) References Cited

U.S. PATENT DOCUMENTS

| 4,637,388 A | 1/1987 | Melendy |
| 5,620,456 A | 4/1997 | Sauer et al. |
| 2003/0009185 A1 | 1/2003 | Jessen |

(Continued)

FOREIGN PATENT DOCUMENTS

WO WO-2006103408 A1 10/2006

OTHER PUBLICATIONS

"International Application Serial No. PCT US2017 027202, International Preliminary Report on Patentability dated Oct. 25, 2018", 8 pgs.

(Continued)

*Primary Examiner* — Wade Miles
(74) *Attorney, Agent, or Firm* — Schwegman Lundberg & Woessner, P.A.

(57) ABSTRACT

A trocar assembly and associated methods are shown. Using example devices and methods shown, a surgeon may insert an obturator with a blade portion and a tube portion of a cannula into tissue such as eye tissue. In one state, the blade portions are wider than or equal to outer diameters of the tube portions. This facilitates an incision in tissue such as eye tissue that is wide enough to allow the tube portions to pass through. Because the blade portions are adapted to deform, they may be withdrawn through the inner diameter of the tube portions.

7 Claims, 6 Drawing Sheets

(56) References Cited

U.S. PATENT DOCUMENTS

2008/0142005 A1    6/2008   Schnell
2009/0182367 A1    7/2009   Hickingbotham
2010/0268175 A1   10/2010   Lunsford et al.
2011/0082342 A1    4/2011   Whitman et al.

OTHER PUBLICATIONS

International Application Serial No. PCT/US2017/027202, International Search Report and Written Opinion dated Jul. 14, 2017, 8 pgs.

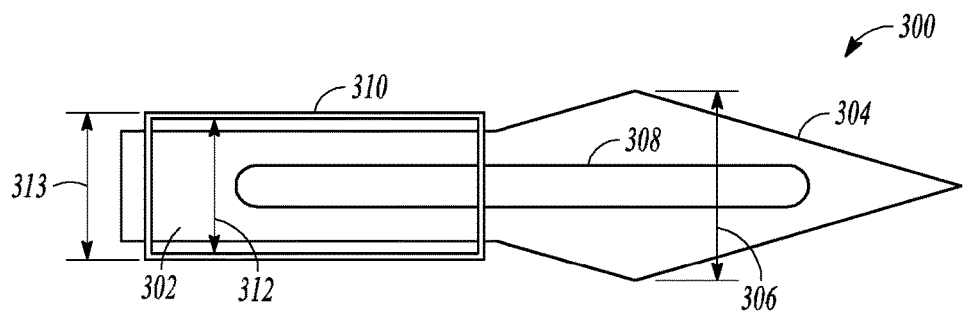
*FIG. 3A*
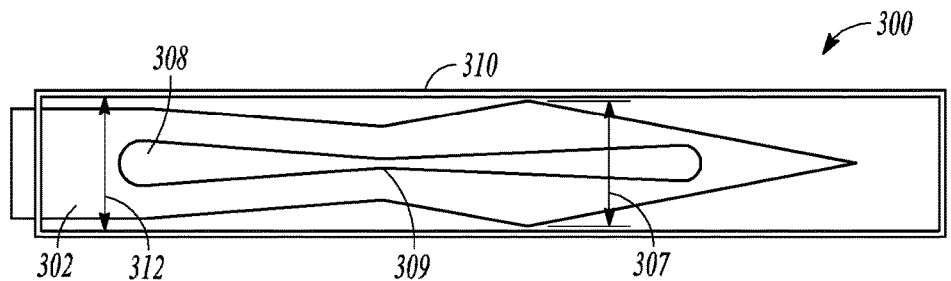
*FIG. 3B*
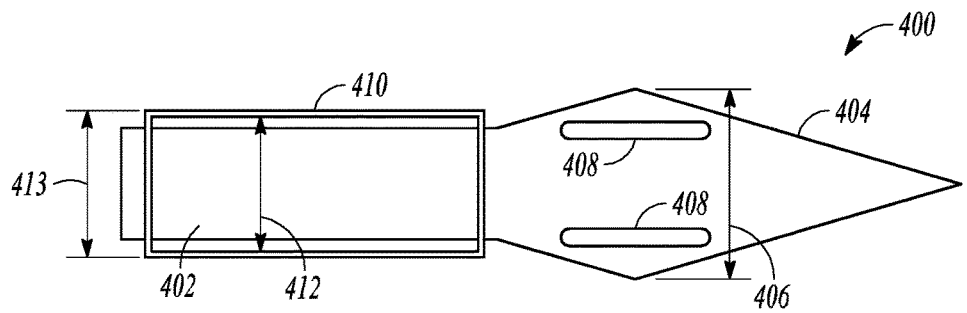
*FIG. 4A*
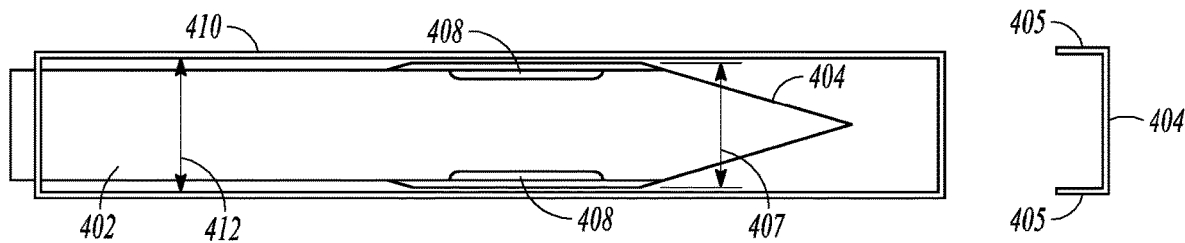
*FIG. 4B*  *FIG. 4C*

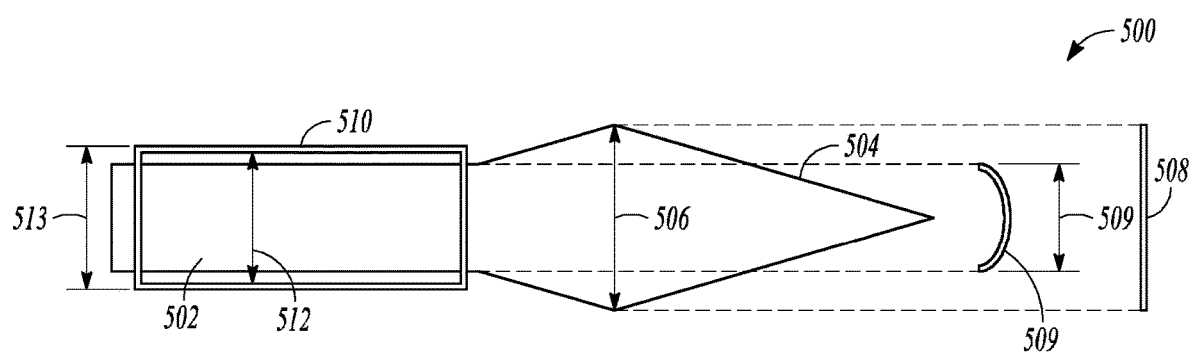
*FIG. 5A*
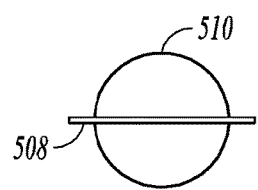
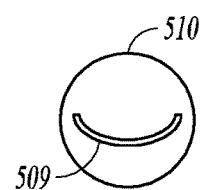
*FIG. 5B*   *FIG. 5C*

TROCAR DEVICE AND METHOD

CLAIM OF PRIORITY

This application is a U.S. National Stage Filing under 35 U.S.C. 371 from International Application No. PCT/US2017/027202 A1, filed on Apr. 12, 2017, and published as WO 2017/180739 A1 on Oct. 19, 2017, which claims the benefit of priority to U.S. Provisional patent application Ser. No. 62/321,571, filed on Apr. 12, 2016, each of which is incorporated by reference herein in its entirety.

TECHNICAL FIELD

This invention relates to devices and methods for insertion of a cannula.

BACKGROUND

A number of ophthalmological procedures require insertion of a cannula into an eye. Use of a cannula allows insertion and removal of instruments through a single opening, without making additional incisions. Existing technologies for insertion of a cannula use a blade to make an incision, however the blade is often smaller than an inner diameter of the cannula being placed. This can lead to a less precise fit between the incision and the cannula than is desired. Improved devices and procedures are desired to place cannulas into an eye.

BRIEF DESCRIPTION OF THE DRAWINGS

FIG. 3A-3B shows a trocar device blade according to an embodiment of the invention.

FIG. 4A-4C shows a trocar device blade according to an embodiment of the invention.

FIG. 5A-5C shows a trocar device blade according to an embodiment of the invention.

DETAILED DESCRIPTION

Figure 1A:
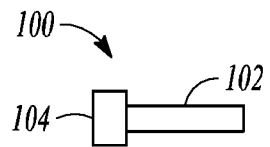
FIG. 1A-1C shows a trocar device according to the prior art.

In the following detailed description, reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, or logical changes, etc. may be made without departing from the scope of the present invention.

Figure 1B:
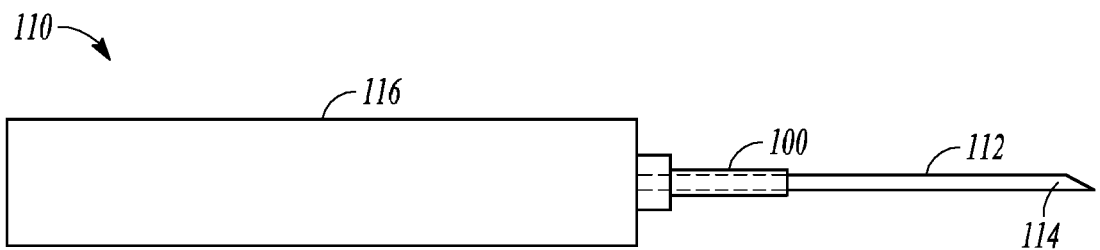
Figure 1C:
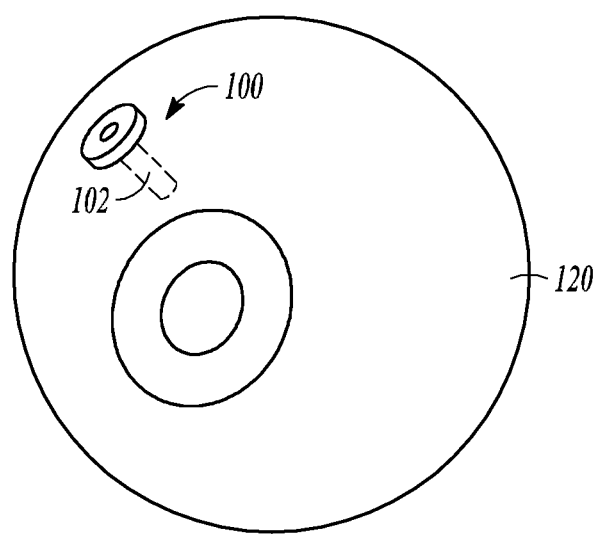

FIG. 1A shows an example of a cannula 100. The cannula includes a tube 102 and a cap 104. FIG. 1B shows the cannula 100 when used with a trocar placement tool 110. The obturator may be used to place the cannula 100 into an eye or other cavity for use in a surgical procedure. The trocar placement tool 110 includes an obturator 112 and a handle 116. In the example shown, the obturator 112 includes a tip 114. In the example shown, the tip 114 includes a blade that is used to make an incision to place the cannula 100. FIG. 1C shows an example with the cannula 100 inserted into an eye 120. The tube portion 102 of the cannula 100 is placed within the eye 120, while the cap portion 104 remains outside the eye 120 and butts up against an outer surface of the eye 120.

Figure 2:
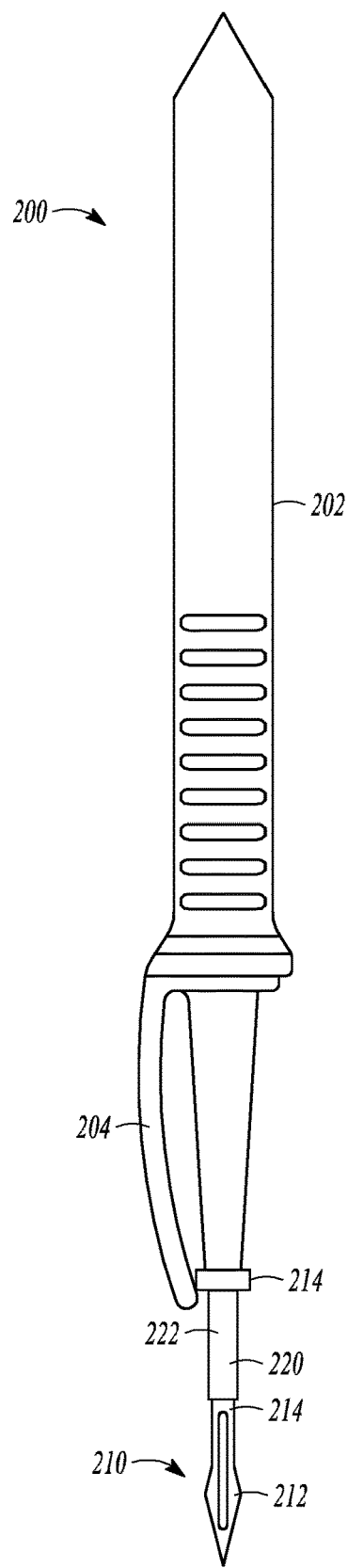
FIG. 2 shows a trocar device according to an embodiment of the invention.

FIG. 2 shows another example of a trocar placement tool 200. In the example of FIG. 2, the trocar placement tool 200 includes a handle 202, and a gripper 204 that may be used to hold a cannula 220. Although a single gripper 204 is shown, two or more grippers may also be included. In the example shown, the cannula 220 is similar in size and shape to the example cannula 100 shown in FIGS. 1A-1C. The cannula 220 is shown with a tube portion 222 and a cap portion 224.

An obturator 210 is shown in FIG. 2 with a portion 214 that has an outer diameter sized to fit within an inner diameter of the cannula 220. The obturator 210 of FIG. 2 further shows a blade 212 at a tip of the obturator 210. The blade 212 is shown with a width that is wider than the inner diameter of the tube portion 222. In the example shown, the blade 212 further includes a width that is wider than an outer diameter of the tube portion 222 of the cannula 220. In one example, the blade 212 is a flexible blade as described in examples below.

FIG. 3A shows one example of a trocar assembly 300 according to an embodiment of the invention. The trocar assembly 300 is shown in a first state that may be used for insertion of a cannula. The trocar assembly 300 includes a shaft portion 302 and a blade portion 304 of an obturator. The blade portion 304 is shown having a first width 306 in an non-deformed state. FIG. 3A further shows a tube portion 310 of a cannula located around the shaft portion 302. In the first state, as illustrated in FIG. 3A, the first width 306 of the blade 304 is wider than an inner diameter 312 of the tube portion 310. In one example in the first state, as illustrated in FIG. 3A, the first width 306 of the blade 304 is also wider than an outer diameter 313 of the tube portion 310. In one example (not shown) in the first state the first width 306 of the blade 304 may be equal to an outer diameter 313 of the tube portion 310.

In the example shown, the blade 304 includes a cut out 308 that enhances an ability for the blade 304 to deform in a controlled manner. FIG. 3B shows the trocar assembly 300 in a second state during removal of the obturator. The blade 304 is in a deformed state where the blade 304 now exhibits a second width 307. As illustrated in FIG. 3B, the second width is smaller or equal to the inner diameter 312 of the tube portion 310. Although any of a number of geometries of cut outs 308 may be used, in the example shown in FIG. 3B, the cut out 308 deforms at a location 309 to allow a wide portion of the blade 304 to deform to within the second width 307.

In one example, the cut out 308 facilitates deformation of the blade portion 304 from the first width 306 to the second width 307. Other examples may include a flexible blade portion 304 that does not utilize cut outs to enhance deformation, but otherwise utilizes thin blade material to permit deformation. In the example shown in FIG. 3B, the deformation of the blade 304 is axial deformation. Other types of deformation may be used in other embodiments of the invention, as discussed below and shown in additional figures.

FIG. 4A shows another example of a trocar assembly 400 according to an embodiment of the invention. The trocar assembly 400 is shown in a first state that may be used for insertion of a cannula. The trocar assembly 400 includes a shaft portion 402 and a blade portion 404 of an obturator. The blade portion 404 is shown having a first width 406 in an non-deformed state. FIG. 4A further shows a tube portion 410 of a cannula located around the shaft portion 402. In the first state, as illustrated in FIG. 4A, the first width 406 of the blade 404 is wider than an inner diameter 412 of the tube portion 410. In one example in the first state, as illustrated in FIG. 4A, the first width 406 of the blade 304 is also wider than an outer diameter 413 of the tube portion 410. In one example (not shown) in the first state the first width 406 of the blade 404 may be equal to an outer diameter 413 of the tube portion 410.

In the example shown, the blade 404 includes a multiple cut outs 408 that enhance an ability for the blade 404 to deform in a controlled manner. FIG. 4B shows the trocar assembly 400 in a second state during removal of the obturator. The blade 404 is in a deformed state where the blade 404 now exhibits a second width 407. As illustrated in FIG. 4B, the second width is smaller or equal to the inner diameter 412 of the tube portion 410. In contrast to the example of FIGS. 3A-3B, the cut outs 408 of blade 404 facilitate flexion upwards (or downwards) out of a plane of the blade 304. FIG. 4C shows an end view of the blade 404 with portions 405 is a deformed state, flexed out of a plane of blade 404.

Similar to the example of FIGS. 3A-3B, examples of the invention are not limited to configurations that include cut outs 408. Other examples may include a flexible blade portion 404 that does not utilize cut outs to enhance deformation, but otherwise utilizes thin blade material to permit deformation.

FIG. 5A shows one example of a trocar assembly 500 with a flexible blade that does not include a cutout according to an embodiment of the invention. The trocar assembly 500 is shown in a first state that may be used for insertion of a cannula. The trocar assembly 500 includes a shaft portion 502 and a blade portion 504 of an obturator. The blade portion 504 is shown having a first width 506 in an non-deformed state. End view illustration 508 also shows the non-deformed state.

FIG. 5A further shows a tube portion 510 of a cannula located around the shaft portion 502. In the first state, as illustrated in FIG. 5A, the first width 506 of the blade 504 is wider than an inner diameter 512 of the tube portion 510. In one example in the first state, as illustrated in FIG. 5A, the first width 506 of the blade 504 is also wider than an outer diameter 513 of the tube portion 510. In one example (not shown) in the first state the first width 506 of the blade 504 may be equal to an outer diameter 513 of the tube portion 510.

End view illustration 509 shows the blade 504 in a second state during removal of the obturator. The blade 504 is in a deformed state where the blade 504 now exhibits a second width 507. The second width 507 is smaller or equal to the inner diameter 512 of the tube portion 510. The example of FIGS. 5A-5C shows another example of flexion out of a plane of the blade 304. End view 509 illustrates a distributed flexing gradient across substantially all of the blade 504. The blade 504 is shown with a substantially smooth curve.

FIG. 5B shows an end view of the blade 504 that further illustrates the tube portion 510. In FIG. 5B, the blade 504 is in an non-deformed state, and the end view 508 is wider than an inner diameter 512 of the tube portion 510. In this example the blade 504 is also wider that the outer diameter 513 of the tube portion 510. FIG. 5C shows an end view of the blade 504 in a deformed state, flexed out of a plane of blade 504, and the end view 509 is thinner than the inner diameter 512 of the tube portion 510.

In operation, a surgeon may insert an obturator with a blade portion similar to blade portions 304, 404, and 504 and shaft portions similar to shaft portions 310, 410, and 510 into tissue such as eye tissue. In one state, as described above, the blade portions 304, 404, and 504 are wider than or equal to outer diameters of the tube portions 310, 410, and 510. This facilitates an incision in tissue such as eye tissue that is wide enough to allow the tube portions 310, 410, and 510 to pass through. Because the blade portions 304, 404, and 504 are flexible, and are adapted to deform, they may be withdrawn through the inner diameter of the tube portions 310, 410, and 510.

Figure 6A:
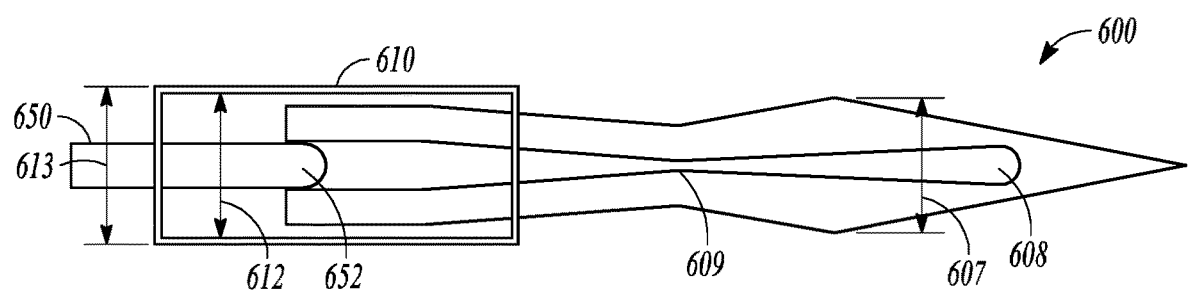
FIG. 6A-6B shows a trocar device blade according to an embodiment of the invention.
Figure 6B:
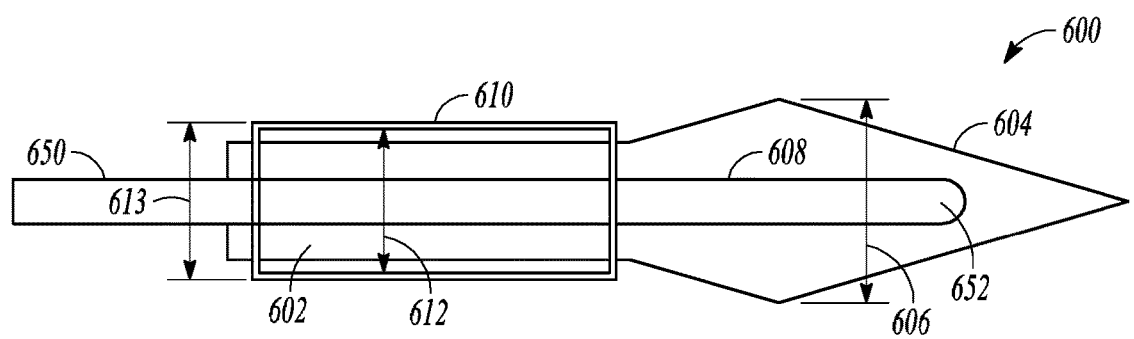

FIGS. 6A and 6B show a trocar assembly 600 according to another example of the invention. The assembly 600 includes a shaft portion 602 and a blade portion 604 of an obturator. In FIG. 6A, the blade portion 604 is shown having a first width 607 in an non-deformed state. In FIGS. 6A and 6B, the non-deformed state provides the first width 607 that is smaller or equal to an inner diameter 612 of a tube portion 610.

In the example of FIG. 6A, the blade portion 604 includes an internal space 608 that is normally compressed at location 609. The compression at location 609 allows the width 607 of the blade portion 604 to be smaller or equal to the inner diameter 612 of the tube portion 610. Although one possible configuration of a compression 609 is shown, other locations and/or configurations of compression features or constrictions are within the scope of the invention.

As in other examples presented above, the blade portion 604 is a flexible blade portion. FIG. 6A further shows a dilator 650 adapted to fit within the internal space 608 within the blade portion 604. As a tip 652 of the dilator 650 enters the internal space 608 of the blade portion 604, the internal space 608 is expanded to a deformed state shown in FIG. 6B. In FIG. 6B, with the dilator 650 inserted within the internal space 608, the blade portion 604 is deformed or otherwise expanded to a second width 606. As illustrated in FIG. 6B, the second width 606 of the blade 604 is wider than an inner diameter 612 of the tube portion 610. In one example, as illustrated in FIG. 6B, the second width 606 of the blade 604 is also wider than an outer diameter 613 of the tube portion 610. In one example (not shown) the second width 606 of the blade 604 may be equal to an outer diameter 613 of the tube portion 610.

In operation, a surgeon may insert the obturator with the blade portion 604 and the shaft portion 620 inside the tube portion. Because the blade portion is in the non-deformed state shown in FIG. 6A, the obturator will slide through the tube portion 610. Then the dilator 650 may be inserted into the internal space 608 of the blade portion 604. This will deform the blade portion 604 to the second width 606 as shown in FIG. 6B. Now the blade portion 604 is wider than or equal to an outer diameter 613 of the tube portion 610. This facilitates an incision in tissue such as eye tissue that is wide enough to allow the tube portion 610 to pass through.

The surgeon may then remove the dilator 650 from within the blade 604 of the obturator. The blade 604 will once again return to the width 607 that is smaller or equal to the inner diameter 612 of the tube portion 610. The obturator and the blade 604 will thus be easily removed through the tube portion.

This procedure and the devices described allow a procedure to make a wide incision as a result of the temporary increased width 606. This procedure and the devices described also allow the obturator to be withdrawn from within the tube portion 610 with a decreased width 607 after making the incision.

Figure 7:
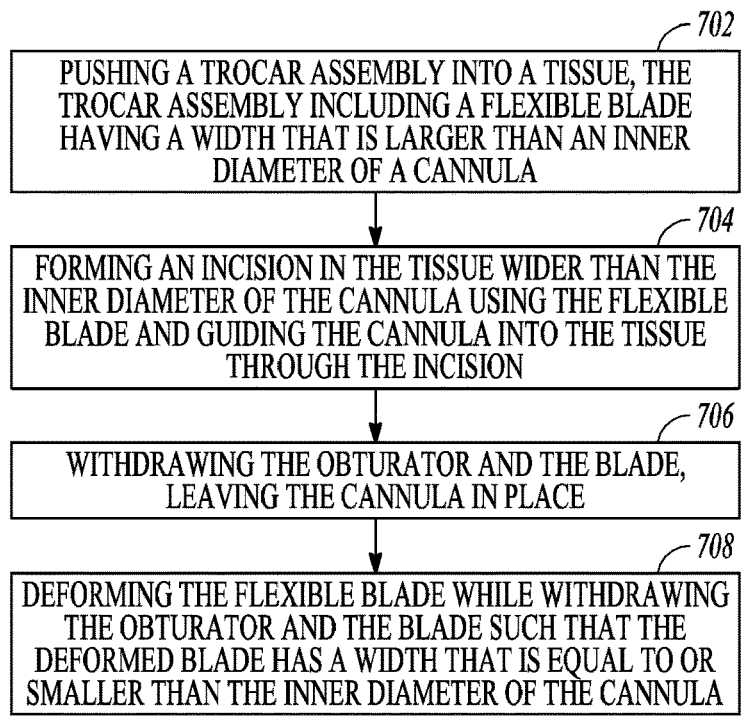
FIG. 7 shows an example method of inserting a trocar according to an embodiment of the invention.

FIG. 7 shows an example method according to one example. In operation 702, a trocar assembly is pushed into a tissue, the trocar assembly including a flexible blade having a width that is larger than an inner diameter of a cannula. In operation 704, an incision is formed in the tissue wider than the inner diameter of the cannula using the flexible blade and guiding the cannula into the tissue through the incision. In operation 706, the obturator and the blade are withdrawn, leaving the cannula in place. In operation 708, the flexible blade is deformed while withdrawing the obturator and the blade such that the deformed blade has a width that is equal to or smaller than the inner diameter of the cannula.

Figure 8:
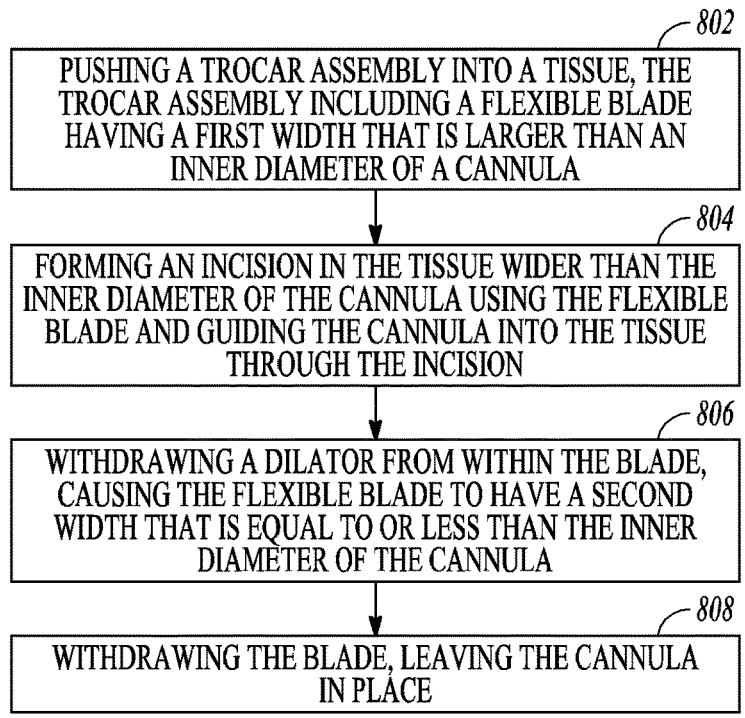
FIG. 8 shows another example method of inserting a trocar according to an embodiment of the invention.

FIG. 8 shows another method according to one example. In operation 802, a trocar assembly is pushed into a tissue, the trocar assembly including a flexible blade at a tip of the obturator. In operation 804, an incision is formed in the tissue wider than the inner diameter of the cannula using the flexible blade and guiding the cannula into the tissue through the incision. In operation 706, a dilator is withdrawn, causing the flexible blade to have a second width that is equal to or less than the inner diameter of the cannula. In operation 708, the obturator and the blade are withdrawn, leaving the cannula in place.

To better illustrate the method and apparatuses disclosed herein, a non-limiting list of embodiments is provided here:

Example 1 includes a trocar assembly. The assembly includes a cannula, an obturator within the cannula, and a flexible blade at a tip of the obturator, the flexible blade having a width that is larger than an inner diameter of the cannula, wherein the flexible blade is adapted to deform sufficiently to allow the obturator to be withdrawn through the inner diameter of the cannula.

Example 2 includes the trocar assembly of example 1, wherein the flexible blade is substantially flat.

Example 3 includes the trocar assembly of any one of examples 1-2, wherein the width is larger than the outer diameter of the cannula.

Example 4 includes the trocar assembly of any one of examples 1-3, wherein the flexible blade is adapted to curl sufficiently to allow the obturator to be withdrawn through the inner diameter of the cannula.

Example 5 includes the trocar assembly of any one of examples 1-4, wherein the flexible blade is adapted to compress axially to allow the obturator to be withdrawn through the inner diameter of the cannula.

Example 6 includes the trocar assembly of any one of examples 1-5, wherein the flexible blade includes one or more cut outs within the blade to enhance flexing.

Example 7 includes the trocar assembly of any one of examples 1-6, wherein the flexible blade includes a central cut out within the blade to enhance flexing.

Example 8 includes the trocar assembly of any one of examples 1-7, wherein the flexible blade includes a pair of side cut outs within the blade to enhance flexing.

Example 9 includes the trocar assembly of any one of examples 1-4, wherein the flexible blade includes a steel blade.

Example 10 includes a trocar assembly. The assembly includes a cannula, an obturator within the cannula, a flexible blade at a tip of the obturator, the flexible blade having an internal space within the blade, and a dilator adapted to fit within the internal space within the blade, wherein a first width of the blade is equal to or wider than an inner diameter of the cannula when the dilator is inserted within the internal space, and wherein a second width of the blade is equal to or smaller than the inner diameter of the cannula when the dilator is removed from the internal space.

Example 11 includes the trocar assembly of example 10, wherein the obturator and the blade are integrally formed.

Example 12 includes the trocar assembly of any one of examples 10-11, wherein the blade is substantially flat.

Example 13 includes the trocar assembly of any one of examples 10-12, wherein the flexible blade includes a steel blade.

Example 14 includes a method of inserting a trocar. The method includes pushing a trocar assembly into a tissue, the trocar assembly including a cannula, an obturator within the cannula, and a flexible blade at a tip of the obturator, the flexible blade having a width that is larger than an inner diameter of the cannula. The method also includes forming an incision in the tissue wider than the inner diameter of the cannula using the flexible blade and guiding the cannula into the tissue through the incision, withdrawing the obturator and the blade, leaving the cannula in place, and deforming the flexible blade while withdrawing the obturator and the blade such that the deformed blade has a width that is equal to or smaller than the inner diameter of the cannula.

Example 15 includes the method of example 14, wherein deforming the flexible blade includes curling the flexible blade.

Example 16 includes the method of any one of examples 14-15, wherein deforming the flexible blade includes axially compressing at least a portion of the blade.

Example 17 includes a method of inserting a trocar. The method includes pushing a trocar assembly into a tissue, the trocar assembly including a cannula, an obturator within the cannula, a flexible blade at a tip of the obturator, and a dilator within the flexible blade causing the flexible blade to have a first width that is larger than an inner diameter of the cannula. The method also includes forming an incision in the tissue wider than the inner diameter of the cannula using the flexible blade and guiding the cannula into the tissue through the incision, withdrawing the dilator, causing the flexible blade to have a second width that is equal to or less than the inner diameter of the cannula, and withdrawing the obturator and the blade, leaving the cannula in place.

Example 18 includes the method of example 17, wherein withdrawing the dilator includes withdrawing the dilator from an internal space within obturator and the blade, wherein the internal space tapers to a more narrow space within the blade.

These and other examples and features of the present infusion devices, and related methods will be set forth in part in the above detailed description. This overview is intended to provide non-limiting examples of the present subject matter—it is not intended to provide an exclusive or exhaustive explanation.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A trocar assembly, comprising:
    a cannula;
    an obturator within the cannula; and
    a flexible blade at a tip of the obturator, the flexible blade having a width that is larger than an inner diameter of the cannula, wherein the flexible blade is adapted to curl sufficiently to allow the obturator to be withdrawn through the inner diameter of the cannula.

2. The trocar assembly of claim 1, wherein the flexible blade is substantially flat.

3. The trocar assembly of claim 1, wherein the width is larger than the outer diameter of the cannula.

4. The trocar assembly of claim 1, wherein the flexible blade is adapted to compress axially to allow the obturator to be withdrawn through the inner diameter of the cannula.

5. The trocar assembly of claim 1, wherein the flexible blade includes a steel blade.

6. A method of inserting a trocar, comprising:
    pushing a trocar assembly into a tissue, the trocar assembly including:
        a cannula;
        an obturator within the cannula;
        a flexible blade at a tip of the obturator, the flexible blade having a width that is larger than an inner diameter of the cannula;
    forming an incision in the tissue wider than the inner diameter of the cannula using the flexible blade and guiding the cannula into the tissue through the incision;
    withdrawing the obturator and the blade, leaving the cannula in place; and
    curling the flexible blade while withdrawing the obturator and the blade such that the curled blade has a width that is equal to or smaller than the inner diameter of the cannula.

7. The method of claim 6, wherein deforming the flexible blade includes axially compressing at least a portion of the blade.

* * * * *